United States Patent
Alataris et al.

(10) Patent No.: US 8,649,874 B2
(45) Date of Patent: Feb. 11, 2014

(54) EXTENDED PAIN RELIEF VIA HIGH FREQUENCY SPINAL CORD MODULATION, AND ASSOCIATED SYSTEMS AND METHODS

(75) Inventors: Konstantinos Alataris, Belmont, CA (US); Andre B. Walker, Monte Sereno, CA (US)

(73) Assignee: Nevro Corporation, Menlo Park, CA (US)

( * ) Notice: Subject to any disclaimer, the term of this patent is extended or adjusted under 35 U.S.C. 154(b) by 41 days.

(21) Appl. No.: 13/308,436

(22) Filed: Nov. 30, 2011

(65) Prior Publication Data

US 2012/0172946 A1 Jul. 5, 2012

Related U.S. Application Data

(60) Provisional application No. 61/418,379, filed on Nov. 30, 2010.

(51) Int. Cl.
*A61N 1/00* (2006.01)

(52) U.S. Cl.
USPC .............................. 607/46; 607/116; 607/117

(58) Field of Classification Search
USPC ........................................... 607/46, 116–117
See application file for complete search history.

(56) References Cited

U.S. PATENT DOCUMENTS

| | | |
|---|---|---|
| 1,597,061 A | 8/1926 | Cultra |
| 2,622,601 A | 12/1952 | Nemec |
| 3,195,540 A | 7/1965 | Waller |
| 3,817,254 A | 6/1974 | Maurer |
| 3,822,708 A | 7/1974 | Zilber |
| 3,893,463 A | 7/1975 | Williams |
| 4,014,347 A | 3/1977 | Halleck et al. |
| 4,023,574 A | 5/1977 | Nemec |
| 4,055,190 A | 10/1977 | Tany et al. |
| 4,414,986 A | 11/1983 | Dickhudt et al. |
| 4,535,777 A | 8/1985 | Castel |
| 4,541,432 A | 9/1985 | Molina-Negro et al. |
| 4,608,985 A | 9/1986 | Crish et al. |
| 4,649,935 A | 3/1987 | Charmillot et al. |

(Continued)

FOREIGN PATENT DOCUMENTS

| | | |
|---|---|---|
| EP | 1181947 A2 | 2/2002 |
| GB | 2449546 A | 11/2008 |

(Continued)

OTHER PUBLICATIONS

International Search Report and Written Opinion for International Patent Application No. PCT/US11/62722, Applicant: Nevro Corporation, mailed Sep. 5, 2012, 9 pages.

(Continued)

*Primary Examiner* — Nicole F Lavert
(74) *Attorney, Agent, or Firm* — Perkins Coie LLP

(57) ABSTRACT

Extended pain relief via high frequency spinal cord modulation, and associated systems and methods. A method for treating a patient in accordance with a particular embodiment includes selecting a neural modulation site to include at least one of a dorsal root entry zone and dorsal horn of the patient's spinal cord, and selecting parameters of a neural modulation signal to reduce patient pain for a period of time after ceasing delivery of the signals, the period of time being at least one tenth of one second.

20 Claims, 9 Drawing Sheets

(56) References Cited

U.S. PATENT DOCUMENTS

| | | |
|---|---|---|
| 4,841,973 A | 6/1989 | Stecker |
| RE33,420 E | 11/1990 | Sussman et al. |
| 5,002,053 A | 3/1991 | Garcia-Rill et al. |
| 5,335,657 A | 8/1994 | Terry, Jr. et al. |
| 5,354,320 A | 10/1994 | Schaldach et al. |
| 5,514,175 A | 5/1996 | Kim et al. |
| 5,562,717 A | 10/1996 | Tippey et al. |
| 5,643,330 A | 7/1997 | Holsheimer et al. |
| 5,716,377 A | 2/1998 | Rise et al. |
| 5,776,170 A | 7/1998 | MacDonald et al. |
| 5,830,151 A | 11/1998 | Hadzic et al. |
| 5,853,373 A | 12/1998 | Griffith et al. |
| 5,893,883 A | 4/1999 | Torgerson et al. |
| 5,983,141 A | 11/1999 | Sluijter et al. |
| 5,995,872 A | 11/1999 | Bourgeois |
| 6,002,964 A | 12/1999 | Feler et al. |
| 6,014,588 A | 1/2000 | Fitz |
| 6,027,456 A | 2/2000 | Feler et al. |
| 6,161,044 A | 12/2000 | Silverstone |
| 6,167,311 A | 12/2000 | Rezai |
| 6,176,242 B1 | 1/2001 | Rise |
| 6,238,423 B1 | 5/2001 | Bardy |
| 6,246,912 B1 | 6/2001 | Sluijter et al. |
| 6,341,236 B1 | 1/2002 | Osorio et al. |
| 6,356,786 B1 | 3/2002 | Rezai et al. |
| 6,405,079 B1 | 6/2002 | Ansarinia |
| 6,421,566 B1 | 7/2002 | Holsheimer |
| 6,440,090 B1 | 8/2002 | Schallhorn |
| 6,505,078 B1 | 1/2003 | King et al. |
| 6,510,347 B2 | 1/2003 | Borkan |
| 6,571,127 B1 | 5/2003 | Ben-Haim et al. |
| 6,584,358 B2 | 6/2003 | Carter et al. |
| 6,609,030 B1 | 8/2003 | Rezai et al. |
| 6,622,048 B1 | 9/2003 | Mann et al. |
| 6,721,603 B2 | 4/2004 | Zabara et al. |
| 6,795,737 B2 | 9/2004 | Gielen et al. |
| 6,856,315 B2 | 2/2005 | Eberlein |
| 6,871,090 B1 | 3/2005 | He et al. |
| 6,885,888 B2 | 4/2005 | Rezai |
| 6,907,295 B2 | 6/2005 | Gross et al. |
| 6,923,784 B2 | 8/2005 | Stein |
| 6,928,230 B2 | 8/2005 | Squibbs |
| 6,928,320 B2 | 8/2005 | King |
| 6,950,707 B2 | 9/2005 | Whitehurst |
| 6,968,237 B2 | 11/2005 | Doan et al. |
| 6,990,376 B2 | 1/2006 | Tanagho et al. |
| 7,024,246 B2 | 4/2006 | Acosta et al. |
| 7,047,079 B2 | 5/2006 | Erickson |
| 7,082,333 B1 | 7/2006 | Bauhahn et al. |
| 7,117,034 B2 | 10/2006 | Kronberg |
| 7,146,224 B2 | 12/2006 | King |
| 7,149,574 B2 | 12/2006 | Yun et al. |
| 7,167,750 B2 | 1/2007 | Knudson et al. |
| 7,180,760 B2 | 2/2007 | Varrichio et al. |
| 7,212,865 B2 | 5/2007 | Cory |
| 7,236,822 B2 | 6/2007 | Dobak, III |
| 7,239,912 B2 | 7/2007 | Dobak, III |
| 7,252,090 B2 | 8/2007 | Goetz |
| 7,260,436 B2 | 8/2007 | Kilgore et al. |
| 7,266,412 B2 | 9/2007 | Stypulkowski |
| 7,288,062 B2 | 10/2007 | Spiegel |
| 7,313,440 B2 | 12/2007 | Miesel |
| 7,324,852 B2 | 1/2008 | Barolat et al. |
| 7,326,181 B2 | 2/2008 | Katims |
| 7,333,857 B2 | 2/2008 | Campbell |
| 7,337,005 B2 | 2/2008 | Kim et al. |
| 7,346,398 B2 | 3/2008 | Gross et al. |
| 7,349,743 B2 | 3/2008 | Tadlock |
| 7,363,076 B2 | 4/2008 | Yun et al. |
| 7,389,145 B2 | 6/2008 | Kilgore et al. |
| 7,393,351 B2 | 7/2008 | Woloszko et al. |
| 7,493,172 B2 | 2/2009 | Whitehurst et al. |
| 7,502,652 B2 | 3/2009 | Gaunt et al. |
| 7,580,753 B2 | 8/2009 | Kim et al. |
| 7,599,737 B2 | 10/2009 | Yomtov et al. |
| 7,676,269 B2 | 3/2010 | Yun et al. |
| 7,689,289 B2 | 3/2010 | King |
| 7,734,340 B2 | 6/2010 | De Ridder |
| 7,742,810 B2 | 6/2010 | Moffitt et al. |
| 7,761,170 B2 | 7/2010 | Kaplan et al. |
| 7,778,704 B2 | 8/2010 | Rezai |
| 7,813,803 B2 | 10/2010 | Heruth et al. |
| 7,826,901 B2 | 11/2010 | Lee et al. |
| 7,860,570 B2 | 12/2010 | Whitehurst et al. |
| 7,877,136 B1 | 1/2011 | Moffitt et al. |
| 7,890,176 B2 | 2/2011 | Jaax et al. |
| 7,933,654 B2 | 4/2011 | Merfeld et al. |
| 7,937,145 B2 | 5/2011 | Dobak |
| 8,010,198 B2 | 8/2011 | Libbus et al. |
| 8,027,718 B2 | 9/2011 | Spinner et al. |
| 8,046,075 B2 | 10/2011 | Rezai |
| 8,060,208 B2 | 11/2011 | Kilgore et al. |
| 8,209,028 B2 | 6/2012 | Skelton et al. |
| 8,255,057 B2 | 8/2012 | Fang et al. |
| 8,355,797 B2 | 1/2013 | Caparso et al. |
| 2002/0055779 A1 | 5/2002 | Andrews |
| 2002/0128700 A1 | 9/2002 | Cross |
| 2003/0120323 A1 | 6/2003 | Meadows et al. |
| 2004/0015202 A1 | 1/2004 | Chandler et al. |
| 2004/0034394 A1 | 2/2004 | Woods et al. |
| 2004/0039425 A1 | 2/2004 | Greenwood-Van Meerveld |
| 2004/0073273 A1 | 4/2004 | Gluckman et al. |
| 2004/0167584 A1 | 8/2004 | Carroll et al. |
| 2004/0210270 A1 | 10/2004 | Erickson |
| 2005/0033381 A1 | 2/2005 | Carter et al. |
| 2005/0038489 A1 | 2/2005 | Grill |
| 2005/0060001 A1 | 3/2005 | Singhal et al. |
| 2005/0113882 A1 | 5/2005 | Cameron et al. |
| 2005/0119713 A1 | 6/2005 | Whitehurst et al. |
| 2005/0143789 A1 | 6/2005 | Whitehurst et al. |
| 2005/0153885 A1 | 7/2005 | Yun et al. |
| 2005/0246006 A1 | 11/2005 | Daniels |
| 2006/0004422 A1 | 1/2006 | De Ridder |
| 2006/0030895 A1 | 2/2006 | Simon et al. |
| 2006/0041285 A1 | 2/2006 | Johnson |
| 2006/0052828 A1 | 3/2006 | Kim et al. |
| 2006/0074456 A1 | 4/2006 | Pyles et al. |
| 2006/0095088 A1 | 5/2006 | De Ridder |
| 2006/0100671 A1 | 5/2006 | Ridder |
| 2006/0161219 A1 | 7/2006 | Mock et al. |
| 2006/0161235 A1 | 7/2006 | King |
| 2006/0190048 A1 | 8/2006 | Gerber |
| 2006/0253182 A1 | 11/2006 | King |
| 2007/0021803 A1 | 1/2007 | Deem et al. |
| 2007/0032827 A1 | 2/2007 | Katims |
| 2007/0039625 A1 | 2/2007 | Heruth et al. |
| 2007/0060954 A1 | 3/2007 | Cameron et al. |
| 2007/0066997 A1 | 3/2007 | He et al. |
| 2007/0073353 A1 | 3/2007 | Rooney et al. |
| 2007/0073354 A1 | 3/2007 | Knudson et al. |
| 2007/0106337 A1 | 5/2007 | Errico et al. |
| 2007/0150034 A1 | 6/2007 | Rooney et al. |
| 2007/0156183 A1 | 7/2007 | Rhodes |
| 2007/0179559 A1 | 8/2007 | Giftakis et al. |
| 2007/0179579 A1 | 8/2007 | Feler et al. |
| 2007/0203537 A1 | 8/2007 | Goetz et al. |
| 2007/0239226 A1 | 10/2007 | Overstreet |
| 2007/0244522 A1 | 10/2007 | Overstreet |
| 2007/0299482 A1 | 12/2007 | Littlewood et al. |
| 2008/0033511 A1 | 2/2008 | Dobak |
| 2008/0103570 A1 | 5/2008 | Gerber |
| 2008/0167697 A1 | 7/2008 | Johnson |
| 2008/0183259 A1 | 7/2008 | Bly et al. |
| 2008/0234791 A1 | 9/2008 | Arle et al. |
| 2009/0036945 A1 | 2/2009 | Chancellor et al. |
| 2009/0054962 A1 | 2/2009 | Lefler et al. |
| 2009/0132010 A1 | 5/2009 | Kronberg |
| 2009/0157141 A1 | 6/2009 | Chiao et al. |
| 2009/0157149 A1 | 6/2009 | Wahlgren et al. |
| 2009/0198306 A1 | 8/2009 | Goetz et al. |
| 2009/0204173 A1* | 8/2009 | Fang et al. ............ 607/46 |
| 2009/0204192 A1 | 8/2009 | Carlton et al. |
| 2009/0281595 A1 | 11/2009 | King et al. |
| 2009/0287274 A1 | 11/2009 | De Ridder |

(56) References Cited

U.S. PATENT DOCUMENTS

| | | |
|---|---|---|
| 2009/0326611 A1 | 12/2009 | Gillbe |
| 2010/0016929 A1 | 1/2010 | Prochazka |
| 2010/0036454 A1 | 2/2010 | Bennett et al. |
| 2010/0069993 A1 | 3/2010 | Greenspan |
| 2010/0094375 A1 | 4/2010 | Donders et al. |
| 2010/0125313 A1 | 5/2010 | Lee et al. |
| 2010/0191307 A1 | 7/2010 | Fang et al. |
| 2010/0241190 A1 | 9/2010 | Kilgore et al. |
| 2010/0249875 A1 | 9/2010 | Kishawi et al. |
| 2010/0274312 A1 | 10/2010 | Alataris et al. |
| 2010/0274314 A1 | 10/2010 | Alataris et al. |
| 2010/0274315 A1 | 10/2010 | Alataris et al. |
| 2010/0274316 A1 | 10/2010 | Alataris et al. |
| 2010/0274317 A1 | 10/2010 | Parker et al. |
| 2010/0274318 A1 | 10/2010 | Walker et al. |
| 2010/0274326 A1 | 10/2010 | Chitre et al. |
| 2010/0324630 A1 | 12/2010 | Lee et al. |
| 2010/0331916 A1 | 12/2010 | Parramon et al. |
| 2011/0009919 A1 | 1/2011 | Carbunaru et al. |
| 2011/0009923 A1 | 1/2011 | Lee |
| 2011/0022114 A1 | 1/2011 | Navarro |
| 2011/0184486 A1 | 7/2011 | De Ridder |
| 2011/0184488 A1 | 7/2011 | De Ridder |
| 2011/0201977 A1 | 8/2011 | Tass |
| 2011/0276107 A1 | 11/2011 | Simon et al. |
| 2011/0282412 A1 | 11/2011 | Glukhovsky et al. |
| 2012/0016437 A1 | 1/2012 | Alataris et al. |
| 2012/0016438 A1 | 1/2012 | Alataris et al. |
| 2012/0016439 A1 | 1/2012 | Alataris et al. |
| 2012/0089200 A1 | 4/2012 | Ranu et al. |
| 2012/0158093 A1 | 6/2012 | Alataris et al. |
| 2012/0197369 A1 | 8/2012 | Alataris et al. |
| 2012/0203303 A1 | 8/2012 | Alataris et al. |
| 2012/0203304 A1 | 8/2012 | Alataris et al. |
| 2012/0203319 A1 | 8/2012 | Alataris et al. |
| 2012/0209349 A1 | 8/2012 | Alataris et al. |
| 2013/0041425 A1 | 2/2013 | Fang et al. |
| 2013/0066411 A1 | 3/2013 | Thacker et al. |
| 2013/0096643 A1 | 4/2013 | Fang et al. |
| 2013/0096644 A1 | 4/2013 | Fang et al. |
| 2013/0110196 A1 | 5/2013 | Alataris et al. |
| 2013/0123879 A1 | 5/2013 | Alataris et al. |
| 2013/0211487 A1 | 8/2013 | Fang et al. |

FOREIGN PATENT DOCUMENTS

| | | |
|---|---|---|
| WO | WO-02065896 A2 | 8/2002 |
| WO | WO-02092165 A1 | 11/2002 |
| WO | WO-2008106174 A1 | 9/2008 |
| WO | WO-2008153726 A2 | 12/2008 |
| WO | WO-2009018518 A1 | 2/2009 |
| WO | WO-2011014570 A1 | 2/2011 |

OTHER PUBLICATIONS

U.S. Appl. No. 13/725,770, filed Dec. 21, 2012, Alataris et al.
U.S. Appl. No. 13/728,965, filed Dec. 27, 2012, Alataris et al.
U.S. Appl. No. 13/830,778, filed Mar. 14, 2013, Alataris et al.
U.S. Appl. No. 13/830,886, filed Mar. 14, 2013, Alataris et al.
U.S. Appl. No. 13/831,057, filed Mar. 14, 2013, Alataris et al.
U.S. Appl. No. 13/620,235, filed Sep. 14, 2012, Alataris et al.
U.S. Appl. No. 13/830,788, filed Mar. 14, 2013, Alataris.
U.S. Appl. No. 13/830,886, filed Mar. 14, 2013, Alataris.
U.S. Appl. No. 13/830,992, filed Mar. 14, 2013, Alataris.
U.S. Appl. No. 13/831,057, filed Mar. 14, 2013, Alataris.
Alo et al., "New Trends in Neuromodulation for the Management of Neuropathic Pain," Neurosurgery, vol. 50, No. 4, Apr. 2002, 15 pages.
Barolat et al., "Multifactorial Analysis of Epidural Spinal Cord Stimulation," Sterotactic and Functional Neurosurgery, 1991; 56: 77-103.
Bhadra et al., "High Frequency electrical conduction block of the pudendal nerve," Journal of Neural Engineering—Institute of Physics Publishing. 2006, 8 pages.
Bhadra MD, Niloy et al., "High-Frequency Electrical Conduction Block of Mammalian Peripheral Motor Nerve," Muscle and Nerve, Dec. 2005, 9 pages.
Boger et al., "Bladder Voiding by Combined High Frequency Electrical Pudendal Nerve Block and Sacral Root Stimulation," Neurourology and Urodynamics, 27, 2008. 5 pages.
Bowman and McNeal, Response of Single Alpha Motoneurons to High-Frequency Pulse Trains, Appl. Neurophysiol. 49, p. 121-138, 1986, 10 pages.
Burton, Charles, "Dorsal Column Stimulation: Optimization of Application," Surgical Neurology, vol. 4, No. 1, Jul. 1975, 10 pages.
DeRidder et al., "Are Paresthesias necessary for pain suppression in SCS—Burst Stimulation," Brain, Brain Research Center Antwerp of Innovative and Interdisciplinary Neuromodulation, 2010, 27 pages.
DeRidder et al., "Burst Spinal Cord Stimulation: Toward Paresthesia-Free Pain Suppression," www.neurosurgery-online.com, vol. 66, Nos. 5, May 2010, 5 pages.
Grill, Warren et al., "Stimulus Waveforms for Selective Neural Stimulation," IEEE Engineering in Medicine and Biology, Jul./Aug. 1995, pp. 375-385.
Holsheimer—Effectiveness of Spinal Cord Stimulation in the Management of Chronic Pain: Analysis of Technical Drawbacks and Solutions, Neurosurgery, vol. 40, No. 5, May 1997, pp. 990-999.
Hopp et al., "Effect of anodal blockade of myelinated fibers on vagal c-fiber afferents," American Journal Physiological Society, Nov. 1980; 239(5), 9 pages.
Hoppenstein, Reuben, "Electrical Stimulation of the Ventral and Dorsal Columns of the Spinal Cord for Relief of Chronic Intractable Pain: Preliminary Report," Surgical Neurology, vol. 4, No. 1, Jul. 1975, 9 pages.
Huxely et al., "Excitation and Conduction in Nerve: Quantitative Analysis," Science, Sep. 11, 1964; 145: 1154-9.
Jang et al., "Analysis of Failed Spinal Cord Stimulation Trails in the Treatment of Intractable Chronic Pain," J. Korean Neurosurg Soc 43, 2008, 5 pages.
Kilgore et al. "Nerve Conduction Block Utilizing High-Frequency Alternating Current" Medical & Biology Engineering and Computing, 2004, vol. 24, pp. 394-406.
Kumar et al., "Spinal Cord Stimulation in Treatment of Chronic Benign Pain: Challenges in Treatment Planning and Present Status, a 22-Year Experience," Neurosurgery, vol. 58, No. 3, Mar. 2006, 16 pages.
Linderoth et al., "Mechanisms of Spinal Cord Stimulation in Painful Syndromes: Role of Animal Models," Pain Medicine, vol. 7, No. S1, 2006, 13 pages.
Linderoth et al., "Physiology of Spinal Cord Stimulation: Review and Update," Neuromodulation, vol. 2, No. 3, 1999, 15 pages.
Mediati, R.D., , "Mechanisms of Spinal Cord Stimulation," Florence, Oct. 2, 2002, 31 pages.
Melzack, Ronald et al., "Pain Mechanisms: A New Theory," Science, vol. 150, No. 3699, Nov. 19, 1965, 9 pages.
Muller and Hunsperger, "Helvetica Physiologica Acta—Reversible Blockierung der Erregungsleitung im Nerven durch Mittelfrequenz-Daverstrom," Schwabe & Co. Basel, vol. 25, Fasc. 1, 1967, 4 pages.
North et al., "Failed Back Surgery Syndrome: 5-year Follow-Up after Spinal Cord Stimulator Implantation," Neurosurgery, Official Journal of the Congress of Neurological Surgeons, vol. 28, No. 5, May 1991, 9 pages.
North et al., "Spinal Cord Stimulation for Axial Low Back Pain," Spine, vol. 30, No. 12, 2005, 7 pages.
North et al., "Spinal Cord Stimulation for Chronic, Intractable Pain: Experience over Two Decades," Neurosurgery, vol. 32, No. 2, Mar. 1993, 12 pages.
Oakley, John C., "Spinal Cord Stimulation Mechanisms of Action," Spine vol. 27, No. 22, copyright 2002, 10 pages.
Shealy MD, C. Norman et al., "Electrical Inhibition of Pain by Stimulation of the Dorsal Columns: Preliminary Clinical Report," Anesthesia and Analgesia . . . Current Researches, vol. 446, No. 4, Jul.-Aug. 1967, 3 pages.
Simpson, BA, "Spinal Cord Stimulation in 60 cases of Intractable Pain." Journal of Neurology, Neurosurgery and Psychiatry, 1991; 54 pp. 196-199.

(56) References Cited

OTHER PUBLICATIONS

Simpson, BA, "Spinal Cord Stimulation." British Journal of Neurosurgery, Feb. 11, 1997, (1), 5-11, 7 pages.
Solomonow et al., "Control of Muscle Contractile Force through Indirect High-Frequency Stimulation," AM Journal of Physical Medicine, 1983, vol. 62, No. 3, pp. 71-82.
Tanner, J.A., "Reversible blocking of nerve conduction by alternating-current excitation," Nature, 1962, Aug. 18; 195: 712-3.
Urban et al., "Percutaneous epidural stimulation of the spinal cord for relief of pain—Long Term Results," Journal of Neurosurgery, vol. 48, Mar. 1978, 7 pages.
Van Den Honert et al. "Generation of Unidirectionally Propagated Action Potentials Nerve by Brief Stimuli" Science, vol. 26, pp. 1311-1312.
Van Den Honert, Mortimer JT, "A Technique for Collison Block of Peripheral Nerve: Frequency Dependence," MP-11 IEEE Trans. Biomed, Eng. 28: 379-382, 1981.
Wolter et al., "Continuous Versus Intermittent Spinal Cord Stimulation: An Analysis of Factors Influencing Clinical Efficacy," Neuromodulation: Technology at Neural Interface, www.neuromodulationjournal.com, 2011, 8 pages.
Woo My, Campbell B. "Asynchronous Firing and Block of Peripheral Nerve Conduction by 20KC Alternating Current," Los Angeles Neuro Society, Jun. 1964; 87-94, 5 pages.
Zhang et al., "Simulation Analysis of Conduction Block in Myelinated Axons Induced by High-Frequency Biphasic Rectangular Pulses," IEEE Transactions on Biomedical Engineering, vol. 53., No. 7, Jul. 2006, 4 pages.
U.S. Appl. No. 13/831,151, filed Mar. 14, 2013, Thacker et al.
U.S. Appl. No. 13/831,241, filed Mar. 14, 2013, Thacker et al.
U.S. Appl. No. 13/831,300, filed Mar. 14, 2013, Thacker et al.
U.S. Appl. No. 13/831,381, filed Mar. 14, 2013, Thacker et al.
Cuellar et al., "Effect of High Frequency Alternating Current ; on Spinal Afferent Nociceptive Transmission," ; Neuromodulation: Technology at the Neural Interface, ; 2012, 10 pages.
Tiede et al., "Novel Spinal Cord Stimulation Parameters ; in Patients with Predominate Back Pain," Neuromodulation:; Technology at the Neural Interface, 2013, 6 pages.
Van Butyen et al., "High Frequency Spinal Cord Stimulation for the ; Treatment of Chronic Back Pain Patients: Results of a Prospective ; Multicenter European Clinical Study," Neuromodulation Technology at the ; Neural Interface, International Neuromodulation Society, 2012, 8 pages.
Perruchoud et al., "Analgesic Efficacy of High-Frequency Spinal Cord Stimulation: A Randomized Double-Blind Placebo-Controlled Study," Neuromodulation: Technology at Neural Interface, International Neuromodulation Society, 2013, 7 pages.
Kilgore et al. "Reversible Nerve Conduction Block Using Kilohertz Frequency Alternating Current," Neuromodulation Technology at the Neural Interface, International Neuromodulation Society, 2013, 13 pages.

* cited by examiner

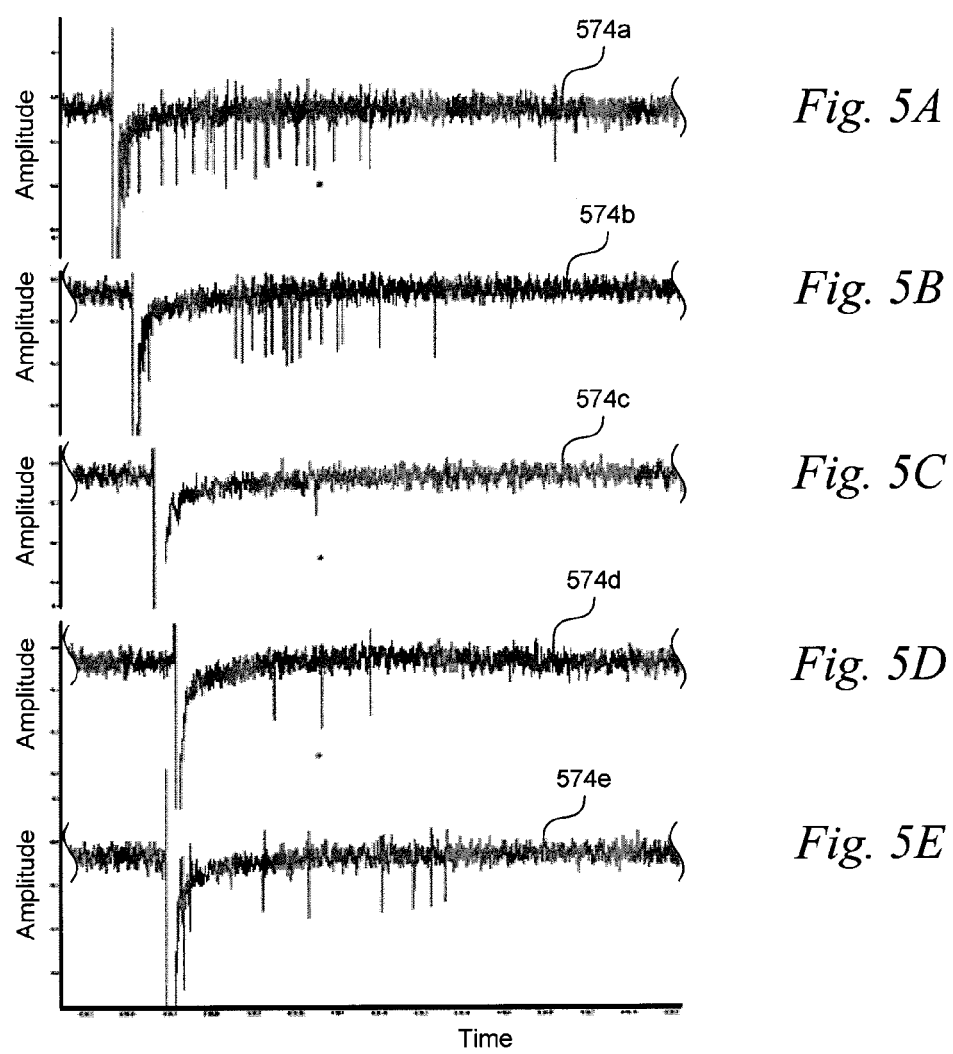

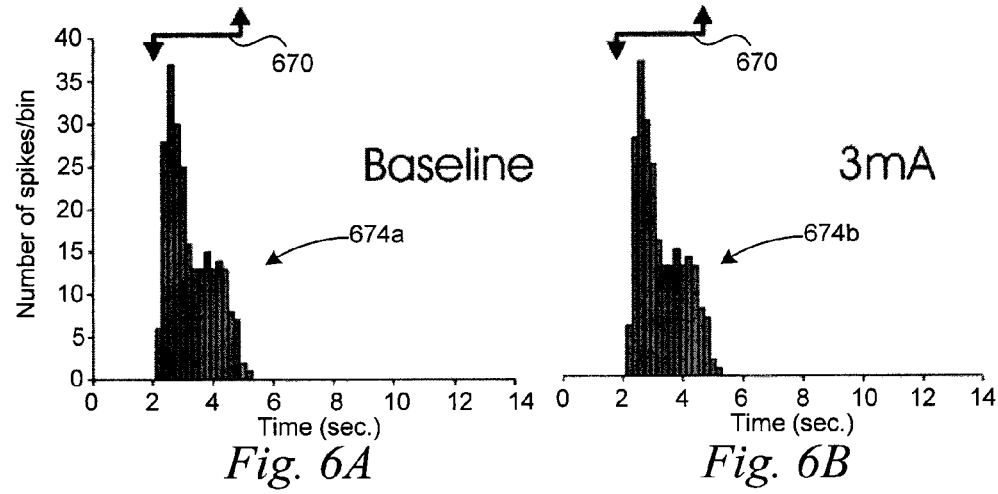
*Fig. 6A*  *Fig. 6B*
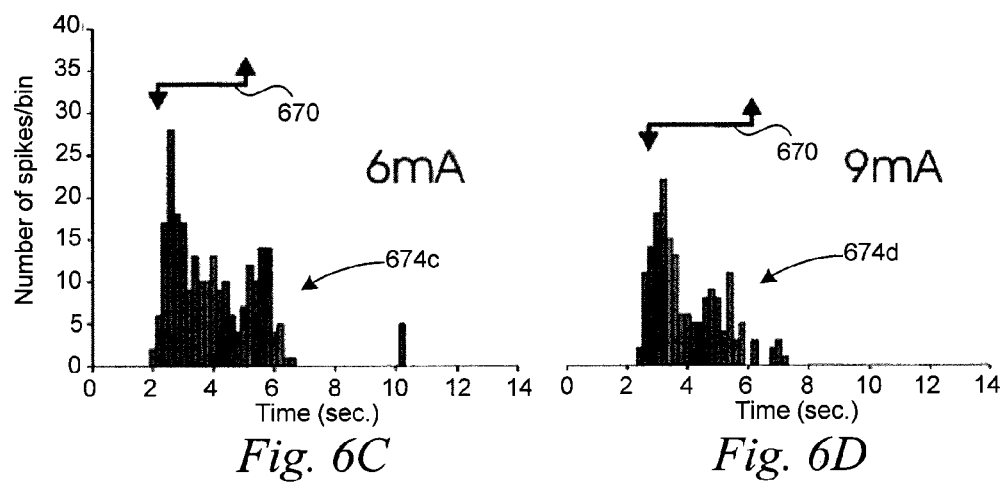
*Fig. 6C*  *Fig. 6D*
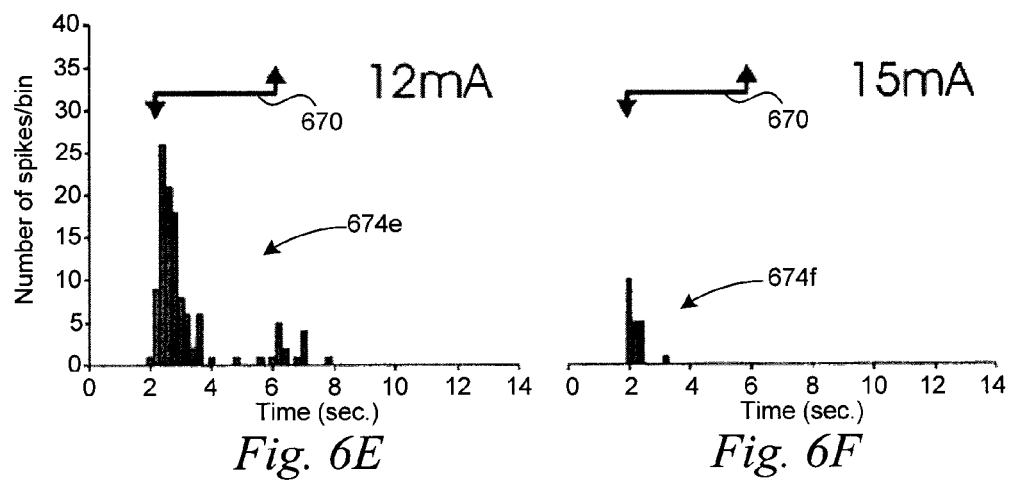
*Fig. 6E*  *Fig. 6F*

US 8,649,874 B2

EXTENDED PAIN RELIEF VIA HIGH FREQUENCY SPINAL CORD MODULATION, AND ASSOCIATED SYSTEMS AND METHODS

CROSS-REFERENCE TO RELATED APPLICATION

The present application claims priority to U.S. Provisional Application No. 61/418,379, filed on Nov. 30, 2010, and incorporated herein by reference.

TECHNICAL FIELD

The present technology is directed generally to extended pain relief obtained via high frequency spinal cord modulation, and associated systems and methods.

BACKGROUND

Neurological stimulators have been developed to treat pain, movement disorders, functional disorders, spasticity, cancer, cardiac disorders, and various other medical conditions. Implantable neurological stimulation systems generally have an implantable pulse generator and one or more leads that deliver electrical pulses to neurological tissue or muscle tissue. For example, several neurological stimulation systems for spinal cord stimulation (SCS) have cylindrical leads that include a lead body with a circular cross-sectional shape and one or more conductive rings spaced apart from each other at the distal end of the lead body. The conductive rings operate as individual electrodes and, in many cases, the SCS leads are implanted percutaneously through a large needle inserted into the epidural space, with or without the assistance of a stylet.

Once implanted, the pulse generator applies electrical pulses to the electrodes, which in turn modify the function of the patient's nervous system, such as by altering the patient's responsiveness to sensory stimuli and/or altering the patient's motor-circuit output. In pain treatment, the pulse generator applies electrical pulses to the electrodes, which in turn can generate sensations that mask or otherwise alter the patient's sensation of pain. For example, in many cases, patients report a tingling or paresthesia that is perceived as more pleasant and/or less uncomfortable than the underlying pain sensation. While this may be the case for many patients, many other patients may report less beneficial effects and/or results. Accordingly, there remains a need for improved techniques and systems for addressing patient pain.

BRIEF DESCRIPTION OF THE DRAWINGS

FIGS. 5A-5E illustrate response data for an animal receiving noxious electrical stimulation and therapy in accordance with an embodiment of the disclosure.

FIGS. 6A-6F illustrate animal response data for animals receiving noxious pinch stimuli in accordance with another embodiment of the disclosure.

DETAILED DESCRIPTION

1.0 Introduction

Figure 1A:
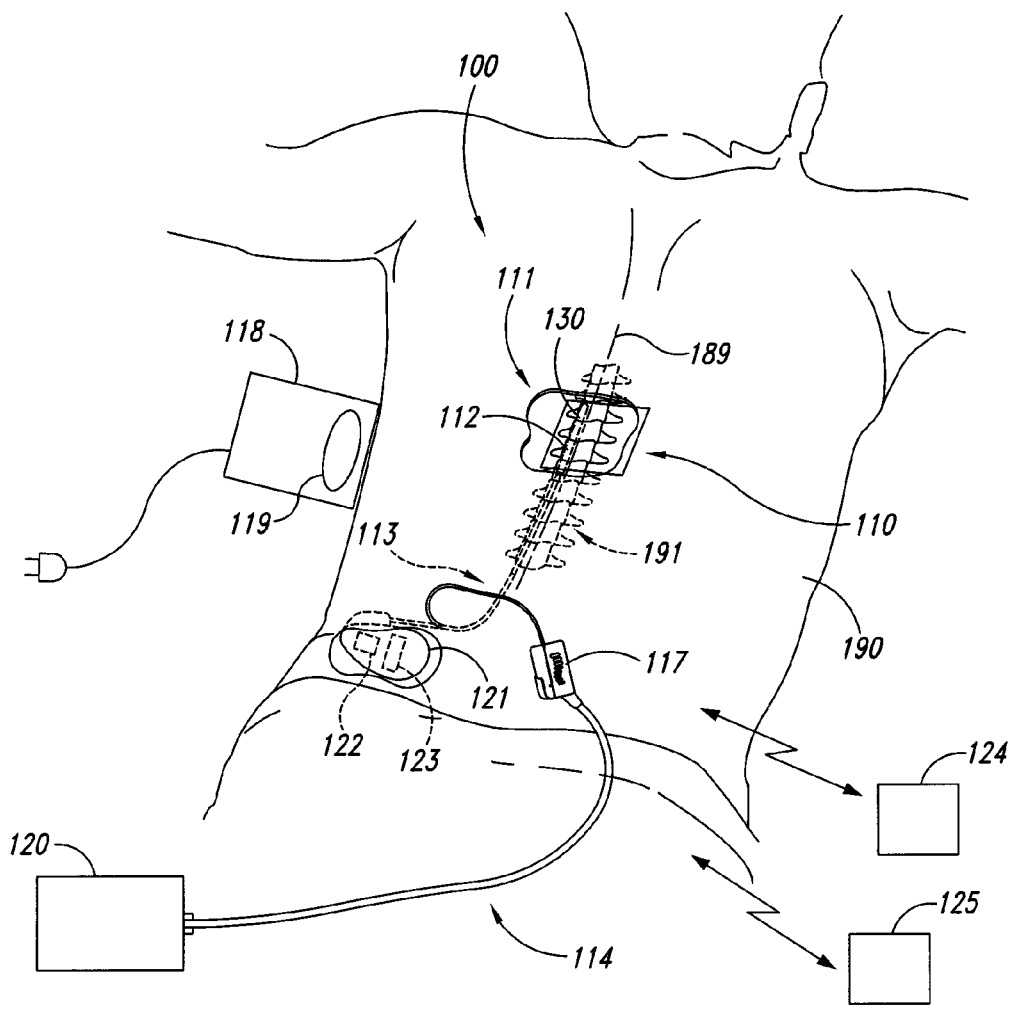
FIG. 1A is a partially schematic illustration of an implantable spinal cord modulation system positioned at the spine to deliver therapeutic signals in accordance with several embodiments of the present disclosure.

The present technology is directed generally to spinal cord modulation and associated systems and methods for inhibiting or otherwise reducing pain via waveforms with high frequency elements or components (e.g., portions having high fundamental frequencies), generally with reduced or eliminated side effects. Such side effects can include unwanted motor stimulation or blocking, and/or interference with sensory functions other than the targeted pain, and/or patient proprioception. Several embodiments continue to provide pain relief for at least some period of time after the spinal cord modulation signals have ceased. Specific details of certain embodiments of the disclosure are described below with reference to methods for modulating one or more target neural populations (e.g., nerves) or sites of a patient, and associated implantable structures for providing the modulation. The following sections also describe physiological mechanisms by which it is expected that methods in accordance with certain embodiments achieve the observed results. Some embodiments can have configurations, components or procedures different than those described in this section, and other embodiments may eliminate particular components or procedures. A person of ordinary skill in the relevant art, therefore, will understand that the disclosure may include other embodiments with additional elements, and/or may include other embodiments without several of the features shown and described below with reference to FIGS. 1A-7.

In general terms, aspects of many of the following embodiments are directed to producing a therapeutic effect that includes pain reduction in the patient. The therapeutic effect can be produced by inhibiting, suppressing, downregulating, blocking, preventing, or otherwise modulating the activity of the affected neural population. In many embodiments of the presently disclosed techniques, therapy-induced paresthesia is not a prerequisite to achieving pain reduction, unlike standard SCS techniques. It is also expected that the techniques described below with reference to FIGS. 1A-7 can produce longer lasting results than can existing spinal cord stimulation therapies. In particular, these techniques can produce results that persist after the modulation signal ceases. Accordingly, these techniques can use less power than existing techniques because they need not require delivering modulation signals continuously to obtain a beneficial effect.

Several aspects of the technology are embodied in computing devices, e.g., programmed/programmable pulse generators, controllers and/or other devices. The computing devices on which the described technology can be implemented may include one or more central processing units, memory, input devices (e.g., input ports), output devices (e.g., display devices), storage devices, and network devices (e.g., network interfaces). The memory and storage devices are computer-readable media that may store instructions that implement the technology. In many embodiments, the computer readable media are tangible media. In other embodiments, the data structures and message structures may be stored or transmitted via an intangible data transmission medium, such as a signal on a communications link. Various suitable communications links may be used, including but not limited to a local area network and/or a wide-area network.

2.0 Overall System Characteristics

FIG. 1A schematically illustrates a representative patient system 100 for providing relief from chronic pain and/or other conditions, arranged relative to the general anatomy of a patient's spinal cord 191. The overall patient system 100 can include a signal delivery system 110, which may be implanted within a patient 190, typically at or near the patient's midline 189, and coupled to a pulse generator 121. The signal delivery system 110 can provide therapeutic electrical signals to the patient during operation. In a representative example, the signal delivery system 110 includes a signal delivery device 111 that carries features for delivering therapy to the patient 190 after implantation. The pulse generator 121 can be connected directly to the signal delivery device 111, or it can be coupled to the signal delivery device 111 via a signal link 113 (e.g., an extension). In a further representative embodiment, the signal delivery device 111 can include an elongated lead or lead body 112. As used herein, the terms "lead" and "lead body" include any of a number of suitable substrates and/or support members that carry devices for providing therapy signals to the patient 190. For example, the lead 112 can include one or more electrodes or electrical contacts that direct electrical signals into the patient's tissue, such as to provide for patient relief. In other embodiments, the signal delivery device 111 can include structures other than a lead body (e.g., a paddle) that also direct electrical signals and/or other types of signals to the patient 190.

The pulse generator 121 can transmit signals (e.g., electrical signals) to the signal delivery device 111 that up-regulate (e.g., stimulate or excite) and/or down-regulate (e.g., block or suppress) target nerves. As used herein, and unless otherwise noted, the terms "modulate" and "modulation" refer generally to signals that have either type of the foregoing effects on the target nerves. The pulse generator 121 can include a machine-readable (e.g., computer-readable) medium containing instructions for generating and transmitting suitable therapy signals. The pulse generator 121 and/or other elements of the system 100 can include one or more processors 122, memories 123 and/or input/output devices. Accordingly, the process of providing modulation signals, providing guidance information for locating the signal delivery device 111, and/or executing other associated functions can be performed by computer-executable instructions contained by computer-readable media located at the pulse generator 121 and/or other system components. The pulse generator 121 can include multiple portions, elements, and/or subsystems (e.g., for directing signals in accordance with multiple signal delivery parameters), carried in a single housing, as shown in FIG. 1A, or in multiple housings.

In some embodiments, the pulse generator 121 can obtain power to generate the therapy signals from an external power source 118. The external power source 118 can transmit power to the implanted pulse generator 121 using electromagnetic induction (e.g., RF signals). For example, the external power source 118 can include an external coil 119 that communicates with a corresponding internal coil (not shown) within the implantable pulse generator 121. The external power source 118 can be portable for ease of use.

During at least some procedures, an external programmer 120 (e.g., a trial modulator) can be coupled to the signal delivery device 111 during an initial procedure, prior to implanting the pulse generator 121. For example, a practitioner (e.g., a physician and/or a company representative) can use the external programmer 120 to vary the modulation parameters provided to the signal delivery device 111 in real time, and select optimal or particularly efficacious parameters. These parameters can include the location from which the electrical signals are emitted, as well as the characteristics of the electrical signals provided to the signal delivery device 111. In a typical process, the practitioner uses a cable assembly 114 to temporarily connect the external programmer 120 to the signal delivery device 111. The practitioner can test the efficacy of the signal delivery device 111 in an initial position. The practitioner can then disconnect the cable assembly 114 (e.g., at a connector 117), reposition the signal delivery device 111, and reapply the electrical modulation. This process can be performed iteratively until the practitioner obtains the desired position for the signal delivery device 111. Optionally, the practitioner may move the partially implanted signal delivery element 111 without disconnecting the cable assembly 114.

After a trial period with the external programmer 120, the practitioner can implant the implantable pulse generator 121 within the patient 190 for longer term treatment. The signal delivery parameters provided by the pulse generator 121 can still be updated after the pulse generator 121 is implanted, via a wireless physician's programmer 125 (e.g., a physician's remote) and/or a wireless patient programmer 124 (e.g., a patient remote). Generally, the patient 190 has control over fewer parameters than does the practitioner.

Figure 1B:
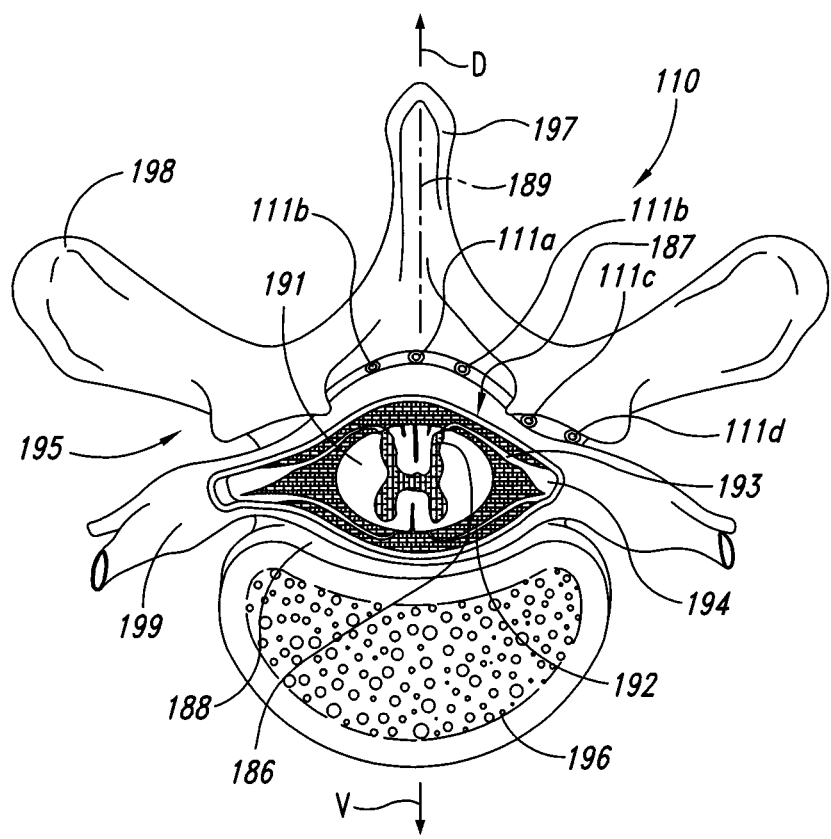
FIG. 1B is a partially schematic, cross-sectional illustration of a patient's spine, illustrating representative locations for implanted lead bodies in accordance with embodiments of the disclosure.

FIG. 1B is a cross-sectional illustration of the spinal cord 191 and an adjacent vertebra 195 (based generally on information from Crossman and Neary, "Neuroanatomy," 1995 (published by Churchill Livingstone)), along with multiple signal delivery devices 111 (shown as signal delivery devices 111a-111d) implanted at representative locations. For purposes of illustration, multiple signal delivery devices 111 are shown in FIG. 1B implanted in a single patient. In actual use, any given patient will likely receive fewer than all the signal delivery devices 111 shown in FIG. 1B.

The spinal cord 191 is situated within a vertebral foramen 188, between a ventrally located ventral body 196 and a dorsally located transverse process 198 and spinous process 197. Arrows V and D identify the ventral and dorsal directions, respectively. The spinal cord 191 itself is located within the dura mater 199, which also surrounds portions of the nerves exiting the spinal cord 191, including the ventral roots 192, dorsal roots 193 and dorsal root ganglia 194. The dorsal roots 193 enter the spinal cord 191 at the dorsal root entry zone 187, and communicate with dorsal horn neurons located at the dorsal horn 186. In one embodiment, a single first signal delivery device 111a is positioned within the vertebral foramen 188, at or approximately at the spinal cord midline 189. In another embodiment, two second signal delivery devices 111b are positioned just off the spinal cord midline 189 (e.g., about 1 mm. offset) in opposing lateral directions so that the two signal delivery devices 111b are spaced apart from each other by about 2 mm. In still further embodiments, a single signal delivery device or pairs of signal delivery devices can be positioned at other locations, e.g., toward the outer edge of the dorsal root entry zone 187 as shown by a third signal delivery device 111c, or at the dorsal root ganglia 194, as shown by a fourth signal delivery device 111d. As will be described in further detail later, it is believed that high frequency modulation at or near the dorsal root entry zone 187, and/or at or near the dorsal horn 186 can produce effective patient pain relief, without paresthesia, without adverse sensory or motor effects, and in a manner that persists after the modulation ceases.

3.0 Representative Results from Human Studies

Nevro Corporation, the assignee of the present application, has conducted several in-human clinical studies during which multiple patients were treated with the techniques, systems and devices that are disclosed herein. Nevro also commissioned animal studies focusing on mechanisms of action for the newly developed techniques. The human clinical studies are described immediately below and the animal studies are discussed thereafter.

Figure 2A:
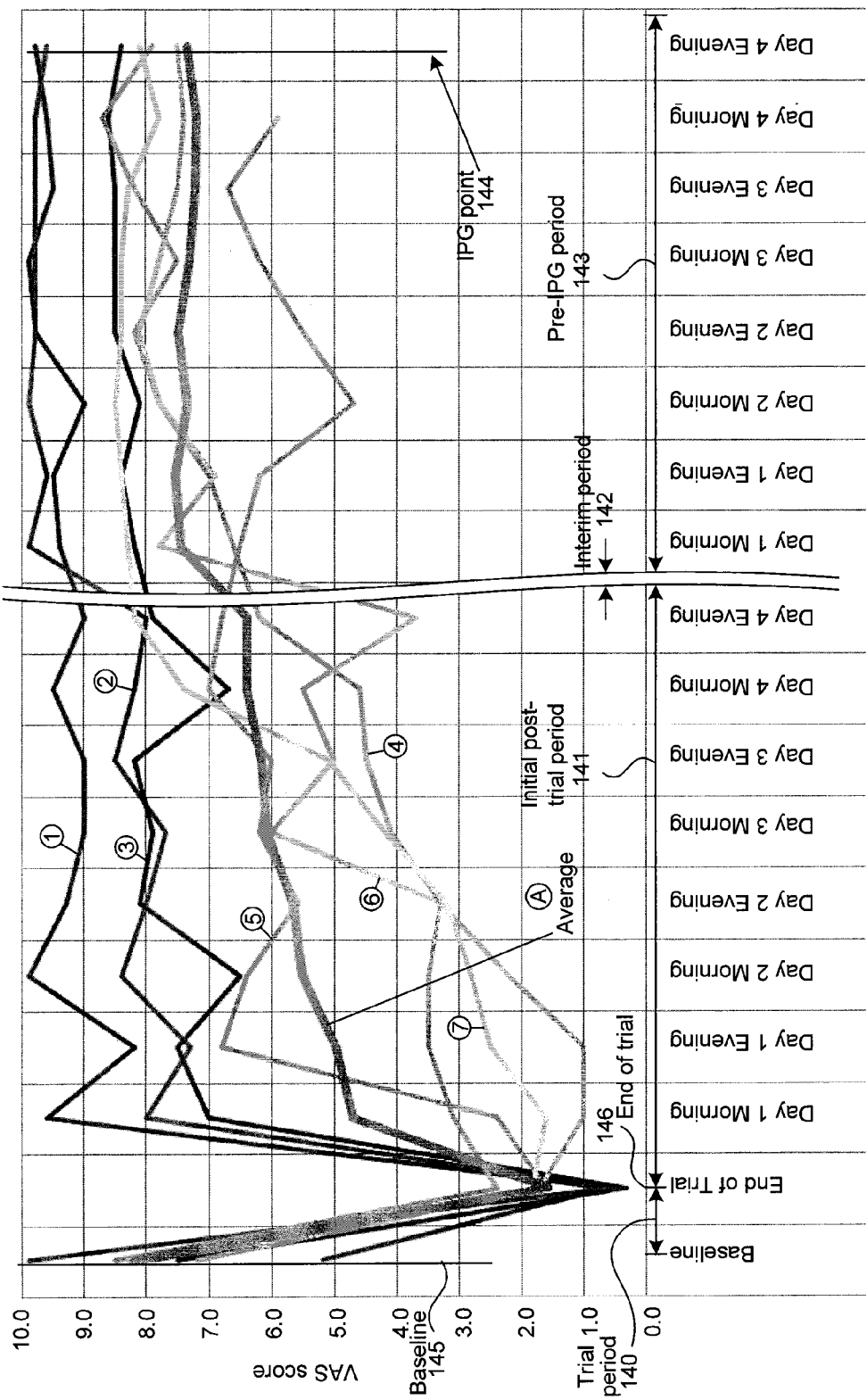
FIG. 2A is a graph illustrating representative patient VAS scores as a function of time for multiple patients receiving therapy in accordance with embodiments of the disclosure.

FIG. 2A is a graph illustrating results from patients who received therapy in accordance with the presently disclosed technology to treat chronic low back pain. In general, the therapy included high-frequency modulation at the patient's spinal cord, typically between vertebral levels T9 and T12 (inclusive), at an average location of mid T10. The modulation signals were applied at a frequency of about 10 kHz, and at current amplitudes of from about 2.5 mA to about 3 mA. Pulse widths were about 35 μsec., at 100% duty cycle. Further details of representative modulation parameters are included in co-pending U.S. patent application Ser. No. 12/765,747, filed on Apr. 22, 2010 and incorporated herein by reference. To the extent the foregoing and/or any other materials incorporated herein by reference conflict with the present disclosure, the present disclosure controls.

The graph shown in FIG. 2A illustrates visual analog scale ("VAS") scores for seven representative patients as a function of time during a clinical study. Individual lines for each patient are indicated with circled numbers in FIG. 2A, and the average is indicated by the circled letter "A". The VAS pain scale ranges from zero (corresponding to no sensed pain) to 10 (corresponding to unbearable pain). At the far left of FIG. 2A are VAS scores taken at a baseline point in time 145, corresponding to the patients' pain levels before receiving any high frequency modulation therapy. During a trial period 140, the patients received a high frequency modulation therapy in accordance with the foregoing parameters and the patients' VAS scores dropped significantly up to an end of trial point 146. In addition, many patients readily reduced or eliminated their intake of pain medications, despite the narcotic characteristics of these medications. During an initial post-trial period 141 (lasting, in this case, four days), the patients' VAS scores increased on average after the high frequency modulation therapy has been halted. The rate at which pain returned after the end of the trial period varied among patients, however, as will be discussed in further detail later. Following the four-day initial post-trial period 141 was an interim period 142 that lasted from about 45 days to about 80 days (depending on the patient), with the average being about 62 days. After the interim period 142, a four-day pre-IPG period 143 commenced ending at an IPG point 144. At the IPG point 144, the patients were implanted with an implantable pulse generator 121, generally similar to that described above with reference to FIG. 1A.

The VAS scores recorded at the baseline 145 and the end of the trial 146 were obtained by the patients recording their levels of pain directly to the practitioner. During the initial post-trial period 141 and the pre-IPG period 143, the patients tracked their VAS score in patient diaries.

Figure 2B:
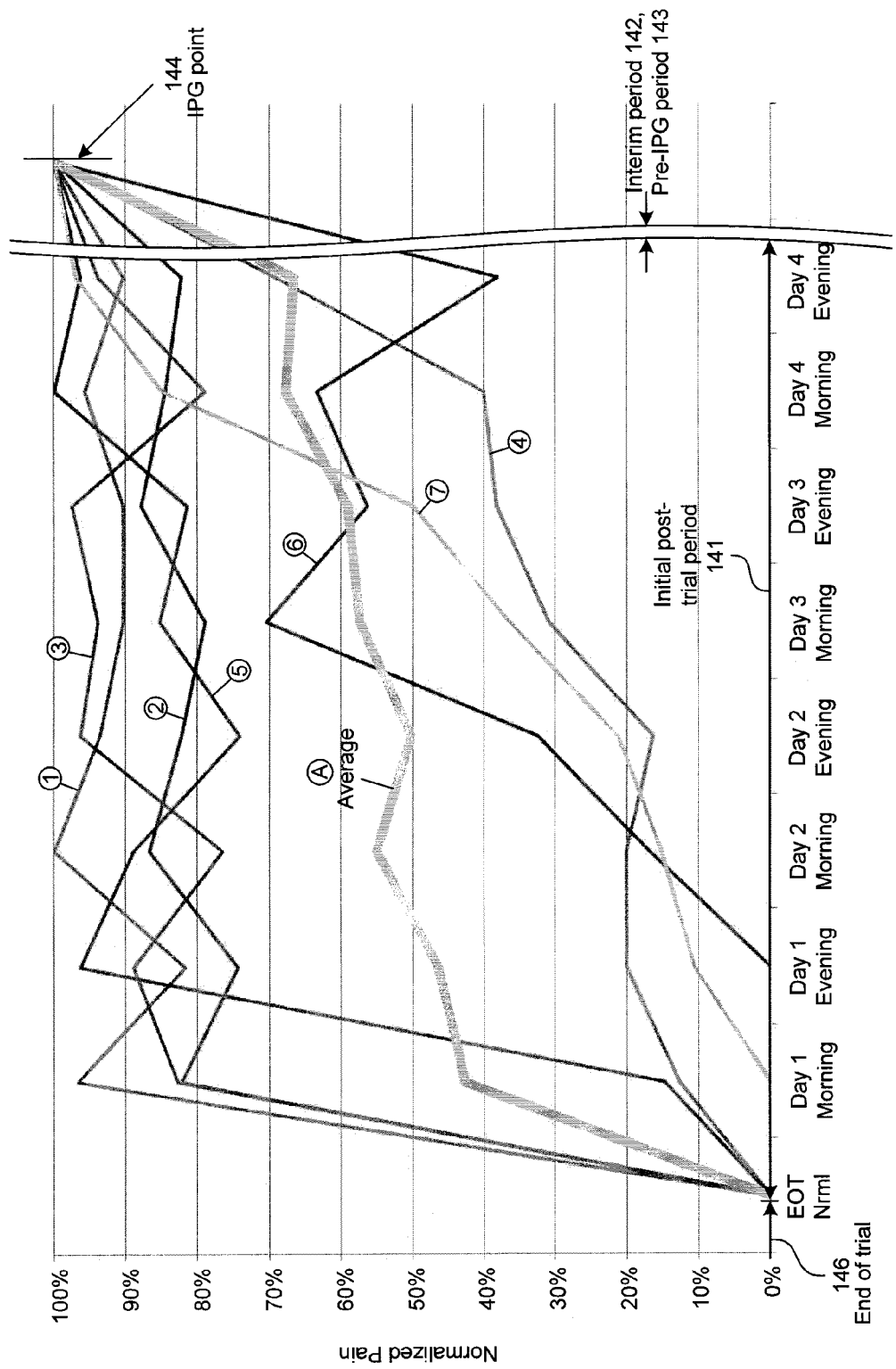
FIG. 2B is a graph illustrating normalized pain scores for the patients identified in FIG. 2A, during an initial post-trial period.

FIG. 2B illustrates data in the initial post-trial period 141 described above with reference to FIG. 2A. For each patient, the pain levels reported in FIG. 2A as VAS scores are shown in FIG. 2B as normalized by evaluating the patient's pain level at the end of trial 146 and at the IPG point 144. Accordingly, for each patient, the normalized pain value is zero at the end of trial 146, and 100% at the IPG point 144. As shown in FIG. 2B, the patients generally fell into two categories: a first group for whom the pain scores rapidly rose from 0% to nearly 100% within a span of about one day after the end of trial 146 (represented by lines 1, 2, 3 and 5); and a second group for whom the pain increase was more gradual, spanning several days before reaching levels above 50% (represented by lines 4, 6 and 7). Accordingly, the data indicate that the patients' pain levels increased compared to the levels obtained at the end of trial 146; however, different patients re-developed pain at different rates. The resolution of the data shown in FIG. 2B is not fine enough to identify precisely how long it took for the patients in the first group to feel a recurrence of high pain levels. However, it was observed by those conducting the studies that the return of the pain for all seven patients was more gradual than is typically associated with standard SCS methodologies. In particular, practitioners having experience with both standard SCS and the presently disclosed technology observed that patients receiving SCS immediately (e.g., within milliseconds) experience a return of pain upon halting the SCS treatment, while the return of pain for patients receiving the presently disclosed therapy was more gradual. Accordingly, it is expected that the persistence effect of the presently disclosed therapy after being administered for two weeks, is likely to be on the order of minutes or hours and, (for many patients), less than one day. It is also believed that the persistence effect may depend at least in part on how long the therapy was applied before it was halted. That is, it is expected that, within a given time period, the longer the patient receives the presently disclosed therapy, the longer the beneficial effect lasts after the therapy signals are halted. Accordingly, it is expected that the presently disclosed therapy can produce effects lasting at least one tenth of one second, at least one second, at least one minute, at least one hour, and/or at least one day, unlike standard SCS techniques, which typically produce effects lasting only milliseconds after the electrical signal ceases. In still further embodiments, it is expected that at least some of the lasting effect described above can be obtained by reducing the intensity (e.g., the current amplitude) of the therapy signal, without ceasing the signal altogether. In at least some embodiments (whether the signal intensity is reduced to zero or to a non-zero value), it is expected that a long enough modulation period can produce a neuroplastic or other change that can last indefinitely, to permanently reduce or eliminate patient pain.

An expected benefit of the persistence or long term effect described above is that it can reduce the need to deliver the therapy signals continuously. Instead, the signals can be delivered intermittently without significantly affecting pain relief. This arrangement can reduce power consumption, thus extending the life of an implanted battery or other power system. It is expected that the power can be cycled according to schedules other than the one explicitly shown in FIGS. 2A and 2B (e.g., other than two weeks on and up to one day off before a significant pain recurrence). The following discussion describes expected potential mechanisms of action by which the presently disclosed therapy operates, including expected mechanisms by which the presently disclosed therapy produces effects persisting after electrical modulation signals have ceased.

4.0 Representative Results from Animal Studies

Figure 3:
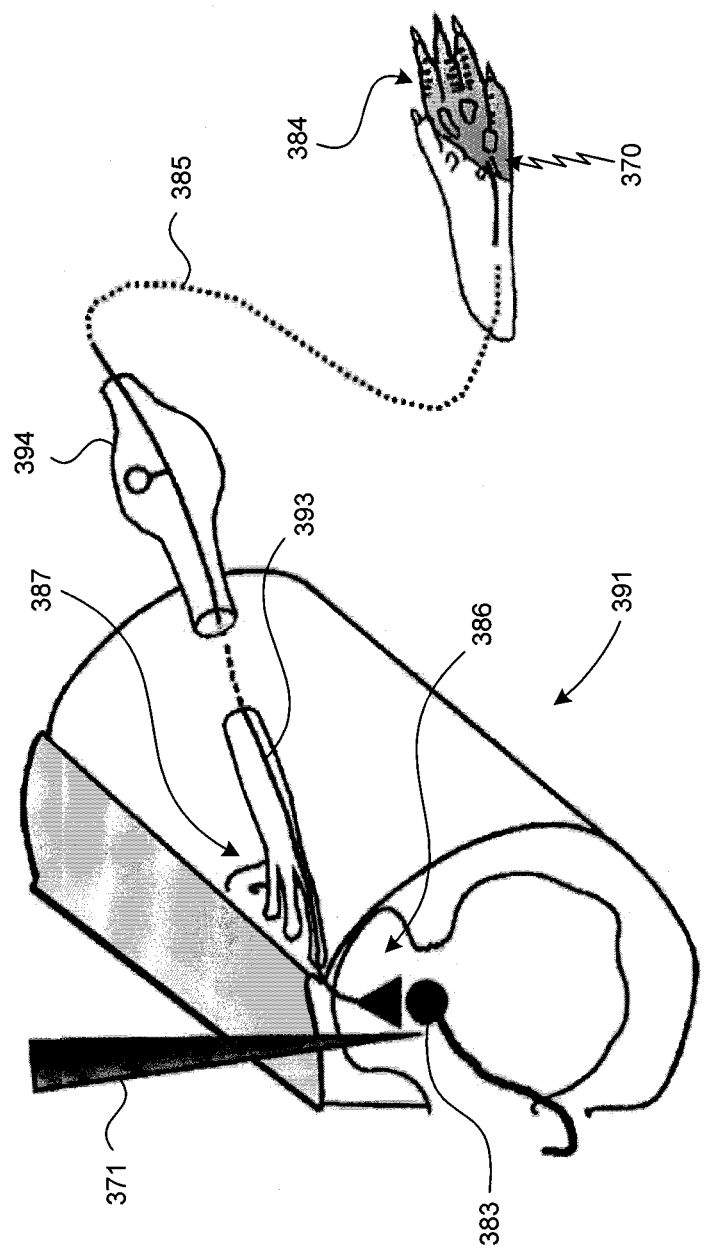
FIG. 3 is a partially schematic, isometric illustration of an animal spinal cord segment and associated nerve structures, used to demonstrate techniques in accordance with the present disclosure.

FIG. 3 is a partially schematic, isometric view of a portion of an animal spinal cord 391 illustrative of a study that was performed on a rat model to illustrate the principles described herein. Accordingly, in this particular embodiment, the illustrated spinal cord 391 is that of a rat. During this study, a noxious electrical stimulation 370 was applied to the rat's hind paw 384. Afferent pain signals triggered by the noxious stimulation 370 traveled along a peripheral nerve 385 to the dorsal root ganglion 394 and then to the dorsal root 393 at the L5 vertebral level. The dorsal root 393 joins the spinal cord 391 at the dorsal root entry zone 387, and transmits afferent signals to a dorsal horn neuron 383 located at the dorsal horn 386. The dorsal horn neuron 383 includes a wide dynamic range ("WDR") cell. An extracellular microelectrode 371 recorded signals transmitted by the dorsal horn neuron 383 to the rat's brain, in response to the noxious stimulation 370 received at the hind paw 384. A therapeutic modulation signal 326 was applied at the dorsal root entry zone 387, proximate to the dorsal horn 386.

Figure 4:
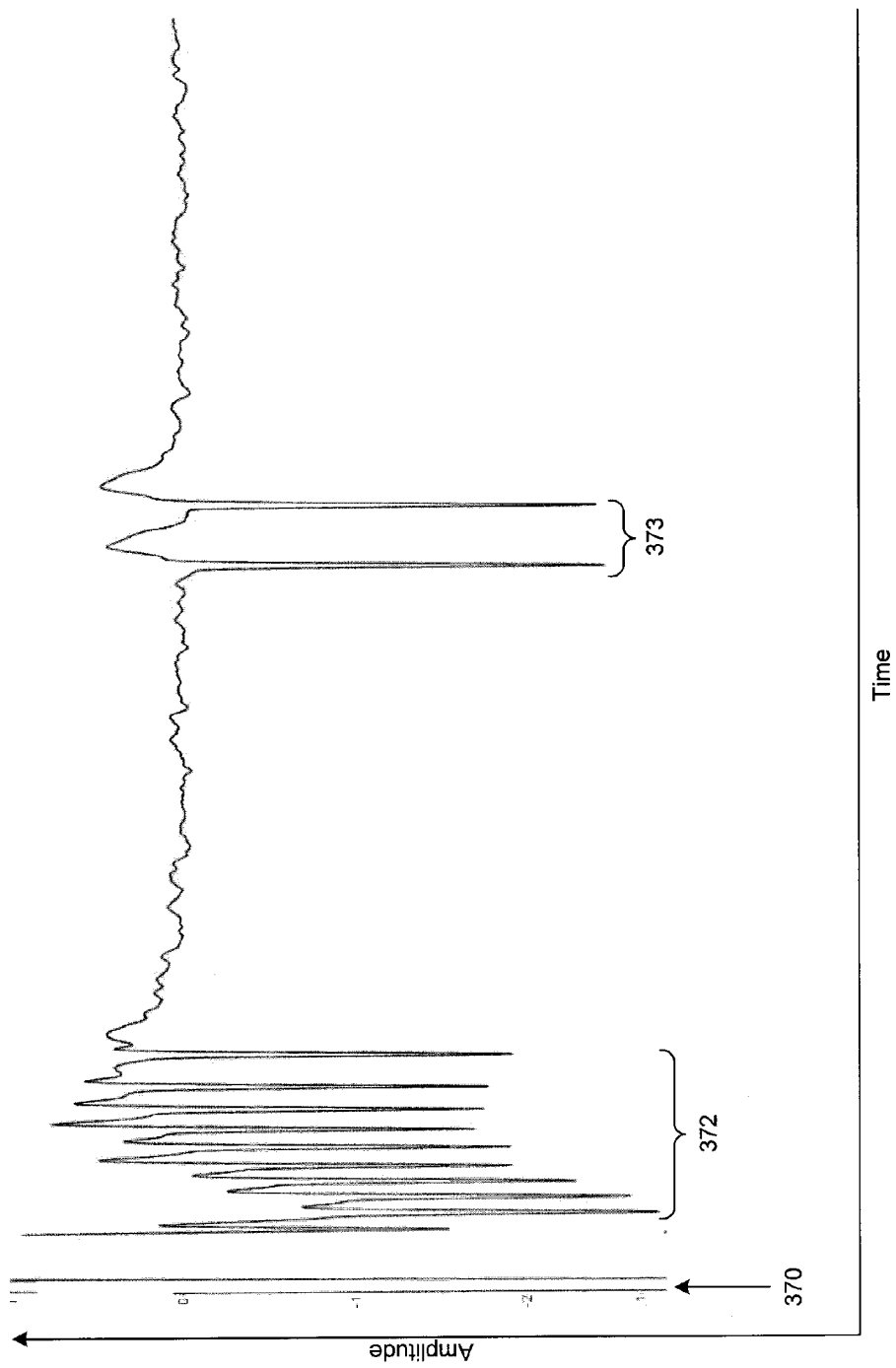
FIG. 4 is a graph illustrating stimulus and response characteristics as a function of time for an animal receiving noxious electrical stimulation in accordance with an embodiment of the disclosure.

FIG. 4 is a graph illustrating neural signal amplitude as a function of time, measured by the recording electrode 371 described above with reference to FIG. 3. FIG. 4 identifies the noxious stimulation 370 itself, the dorsal horn neuron's response to A-fiber inputs 372, and the dorsal horn neuron's response to C-fiber inputs 373. The larger A-fibers trigger an earlier response at the dorsal horn neuron than do the smaller C-fibers. Both responses are triggered by the same noxious stimulus 370. The rat's pain response is indicated by downward amplitude spikes. The foregoing response is a typical response to a noxious stimulus, absent pain modulation therapy.

FIGS. 5A-5E illustrate the dorsal horn neuron response to ongoing noxious stimuli as the applied therapy signal was altered. The signal applied to each rat was applied at a constant frequency, which varied from rat to rat over a range of from about 3 kHz to about 100 kHz. The response data (which were obtained from nine rats) were relatively insensitive to frequency over this range. During the course of this study, the noxious stimuli were provided repeatedly at a constant rate of one stimulus per second over an approximately five-minute period. At the outset of the five-minute period, the therapy signal was turned off, resulting in a baseline response 574*a* shown in FIG. 5A, and then gradually increased as shown in FIG. 5B, to a maximum intensity shown in FIG. 5C. During the period shown in FIG. 5D, the intensity of the therapy signal was reduced, and in FIG. 5E, the therapy signal was turned off. Consistent with the data shown in FIG. 4, the rat's pain response is indicated by downward spikes. The baseline response 574*a* has a relatively large number of spikes, and the number of spikes begins to reduce as the intensity of the modulation signal is increased (see response 574*b* in FIG. 5B). At the maximum therapy signal intensity, the number of spikes has been reduced to nearly zero as indicated by response 574*c* in FIG. 5C. As the therapy signal intensity is then reduced, the spikes begin to return (see response 574*d*, FIG. 5D), and when the modulation signal is turned off, the spikes continue to return (see response 574*e*, FIG. 5E). Significantly, the number of spikes shown in FIG. 5E (10-20 seconds after the therapy has been turned off) is not as great as the number of spikes generated in the baseline response 574*a* shown in FIG. 5A. These data are accordingly consistent with the human trial data described above with reference to FIGS. 2A and 2B, which indicated a beneficial effect lasting beyond the cessation of the therapy signal. These data also differ significantly from results obtained from similar studies conducted with standard SCS. Notably, dorsal horn recordings during standard SCS treatments do not indicate a reduction in amplitude spikes.

FIGS. 6A-6F illustrate animal response data in a rat model to a different noxious stimulus; in particular, a pinch stimulus 670. The pinch stimulus is a mechanical pinch (rather than an electrical stimulus) at the rat's hindpaw. In each succeeding figure in the series of FIGS. 6A-6F, the amplitude of the therapy signal was increased. The levels to which the signal amplitude was increased were significantly higher than for the human study simply due to a cruder (e.g., less efficient) coupling between the signal delivery electrode and the target neural population. The vertical axis of each Figure indicates the number of spikes (e.g., the spike-shaped inputs 372, 373 shown in FIG. 3) per bin; that is, the number of spikes occurring during a given time period. In the particular embodiment shown in FIGS. 6A-6F, each bin has a duration of 0.2 second, so that there are a total of five bins per second, or 10 bins during each two-second period. The pinch stimulus 670 lasts for three to five seconds in each of FIGS. 6A-6F. In FIG. 6A, the baseline response 674*a* indicates a large number of spikes per bin extending over the duration of the pinch stimulus 670. As shown in FIGS. 6B-6F, the number of spikes per bin decreases, as indicated by responses 674*b*-674*f*, respectively. In the final Figure in this series (FIG. 6F), the response 674*f* is insignificant or nearly insignificant when compared with the baseline response 674*a* shown in FIG. 6A.

The foregoing rat data was confirmed in a subsequent study using a large animal model (goat). Based on these data, it is clear that therapy signals in accordance with the present technology reduce pain; further, that they do so in a manner consistent with that observed during the human studies.

Returning now to FIG. 3, it is expected (without being bound by theory) that the therapy signals act to reduce pain via one or both of two mechanisms: (1) by reducing neural transmissions entering the spinal cord at the dorsal root 393 and/or the dorsal root entry zone 387, and/or (2) by reducing neural activity at the dorsal horn 386 itself. It is further expected that the therapy signals described in the context of the rat model shown in FIG. 3 operate in a similar manner on the corresponding structures of the human anatomy, e.g., those shown in FIG. 1B. In particular, it is generally known that chronic pain patients may be in a state of prolonged sensory sensitization at both the nociceptive afferent neurons (e.g., the peripheral nerve 385 and the associated dorsal root 393) and at higher order neural systems (e.g., the dorsal horn neuron 383). It is also known that the dorsal horn neurons 383 (e.g., the WDR cells) are sensitized in chronic pain states. The noxious stimuli applied during the animal studies can result in an acute "windup" of the WDR cells (e.g., to a hyperactive state). In accordance with mechanism (1) above, it is believed that the therapy signals applied using the current technology operate to reduce pain by reducing, suppressing, and/or attenuating the afferent nociceptive inputs delivered to the WDR cells 383, as it is expected that these inputs, unless attenuated, can be responsible for the sensitized state of the WDR cells 383. In accordance with mechanism (2) above, it is expected that the presently disclosed therapy can act directly on the WDR cells 383 to desensitize these cells. In particular, the patients selected to receive the therapy described above with reference to FIGS. 2A-2B included patients whose pain was not correlated with peripheral stimuli. In other words, these patients had hypersensitive WDR cells 383 independent of whether signals were transmitted to the WDR cells 383 via peripheral nerve inputs or not. These patients, along with the other treated patients, experienced the significant pain reductions described above. Accordingly, it is believed that the disclosed therapy can operate directly on the WDR cells 383 to reduce the activity level of hyperactive WDR cells 383, and/or can reduce incoming afferent signals from the peripheral nerve 385 and dorsal root 393. It is further believed that the effect of the presently disclosed therapy on peripheral inputs may produce short term pain relief, and the effect on the WDR cells may produce longer term pain relief. Whether the reduced output of the WDR cells results from mechanism (1), mechanism (2), or both, it is further expected that the high frequency characteristics of the therapeutic signals produce the observed results. In addition, embodiments of the presently disclosed therapy produce pain reduction without the side effects generally associated with standard SCS, as discussed further in co-pending U.S. patent application Ser. No. 12/765,747, filed on Apr. 22, 2010, previously incorporated herein by reference. These and other advantages associated with embodiments of the presently disclosed technology are described further below.

Certain of the foregoing embodiments can produce one or more of a variety of advantages, for the patient and/or the practitioner, when compared with standard SCS therapies. Some of these benefits were described above. For example, the patient can receive beneficial effects from the modulation therapy after the modulation signal has ceased. In addition, the patient can receive effective pain relief without simultaneous paresthesia, without simultaneous patient-detectable disruptions to normal sensory signals along the spinal cord, and/or without simultaneous patient-detectable disruptions to normal motor signals along the spinal cord. In particular embodiments, while the therapy may create some effect on normal motor and/or sensory signals, the effect is below a level that the patient can reliably detect intrinsically, e.g., without the aid of external assistance via instruments or other devices. Accordingly, the patient's levels of motor signaling and other sensory signaling (other than signaling associated with the target pain) can be maintained at pre-treatment levels. For example, the patient can experience a significant pain reduction that is largely independent of the patient's movement and position. In particular, the patient can assume a variety of positions and/or undertake a variety of movements associated with activities of daily living and/or other activities, without the need to adjust the parameters in accordance with which the therapy is applied to the patient (e.g., the signal amplitude). This result can greatly simplify the patient's life and reduce the effort required by the patient to experience pain relief while engaging in a variety of activities. This result can also provide an improved lifestyle for patients who experience pain during sleep.

Even for patients who receive a therapeutic benefit from changes in signal amplitude, the foregoing therapy can provide advantages. For example, such patients can choose from a limited number of programs (e.g., two or three) each with a different amplitude and/or other signal delivery parameter, to address some or all of the patient's pain. In one such example, the patient activates one program before sleeping and another after waking. In another such example, the patient activates one program before sleeping, a second program after waking, and a third program before engaging in particular activities that would otherwise cause pain. This reduced set of patient options can greatly simplify the patient's ability to easily manage pain, without reducing (and in fact, increasing) the circumstances under which the therapy effectively addresses pain. In any embodiments that include multiple programs, the patient's workload can be further reduced by automatically detecting a change in patient circumstance, and automatically identifying and delivering the appropriate therapy regimen. Additional details of such techniques and associated systems are disclosed in co-pending U.S. application Ser. No. 12/703,683, incorporated herein by reference.

Another benefit observed during clinical studies is that when the patient does experience a change in the therapy level, it is a gradual change. This is unlike typical changes associated with conventional SCS therapies. With conventional SCS therapies, if a patient changes position and/or changes an amplitude setting, the patient can experience a sudden onset of pain, often described by patients as unbearable. By contrast, patients in the clinical studies described above, when treated with the presently disclosed therapy, reported a gradual onset of pain when signal amplitude was increased beyond a threshold level, and/or when the patient changed position, with the pain described as gradually becoming uncomfortable. One patient described a sensation akin to a cramp coming on, but never fully developing. This significant difference in patient response to changes in signal delivery parameters can allow the patient to more freely change signal delivery parameters and/or posture when desired, without fear of creating an immediately painful effect.

Another observation from the clinical studies described above is that the amplitude "window" between the onset of effective therapy and the onset of pain or discomfort is relatively broad, and in particular, broader than it is for standard SCS treatment. For example, during standard SCS treatment, the patient typically experiences a pain reduction at a particular amplitude, and begins experiencing pain from the therapeutic signal (which may have a sudden onset, as described above) at from about 1.2 to about 1.6 times that amplitude. This corresponds to an average dynamic range of about 1.4. In addition, patients receiving standard SCS stimulation typically wish to receive the stimulation at close to the pain onset level because the therapy is often most effective at that level. Accordingly, patient preferences may further reduce the effective dynamic range. By contrast, therapy in accordance with the presently disclosed technology resulted in patients obtaining pain relief at 1 mA or less, and not encountering pain or muscle capture until the applied signal had an amplitude of 4 mA, and in some cases up to about 5 mA, 6 mA, or 8 mA, corresponding to a much larger dynamic range (e.g., larger than 1.6 or 60% in some embodiments, or larger than 100% in other embodiments). Even at the forgoing amplitude levels, the pain experienced by the patients was significantly less than that associated with standard SCS pain onset. An expected advantage of this result is that the patient and practitioner can have significantly wider latitude in selecting an appropriate therapy amplitude with the presently disclosed methodology than with standard SCS methodologies. For example, the practitioner can increase the signal amplitude in an effort to affect more (e.g., deeper) fibers at the spinal cord, without triggering unwanted side effects. The existence of a wider amplitude window may also contribute to the relative insensitivity of the presently disclosed therapy to changes in patient posture and/or activity. For example, if the relative position between the implanted lead and the target neural population changes as the patient moves, the effective strength of the signal when it reaches the target neural population may also change. When the target neural population is insensitive to a wider range of signal strengths, this effect can in turn allow greater patient range of motion without triggering undesirable side effects.

Figure 7:
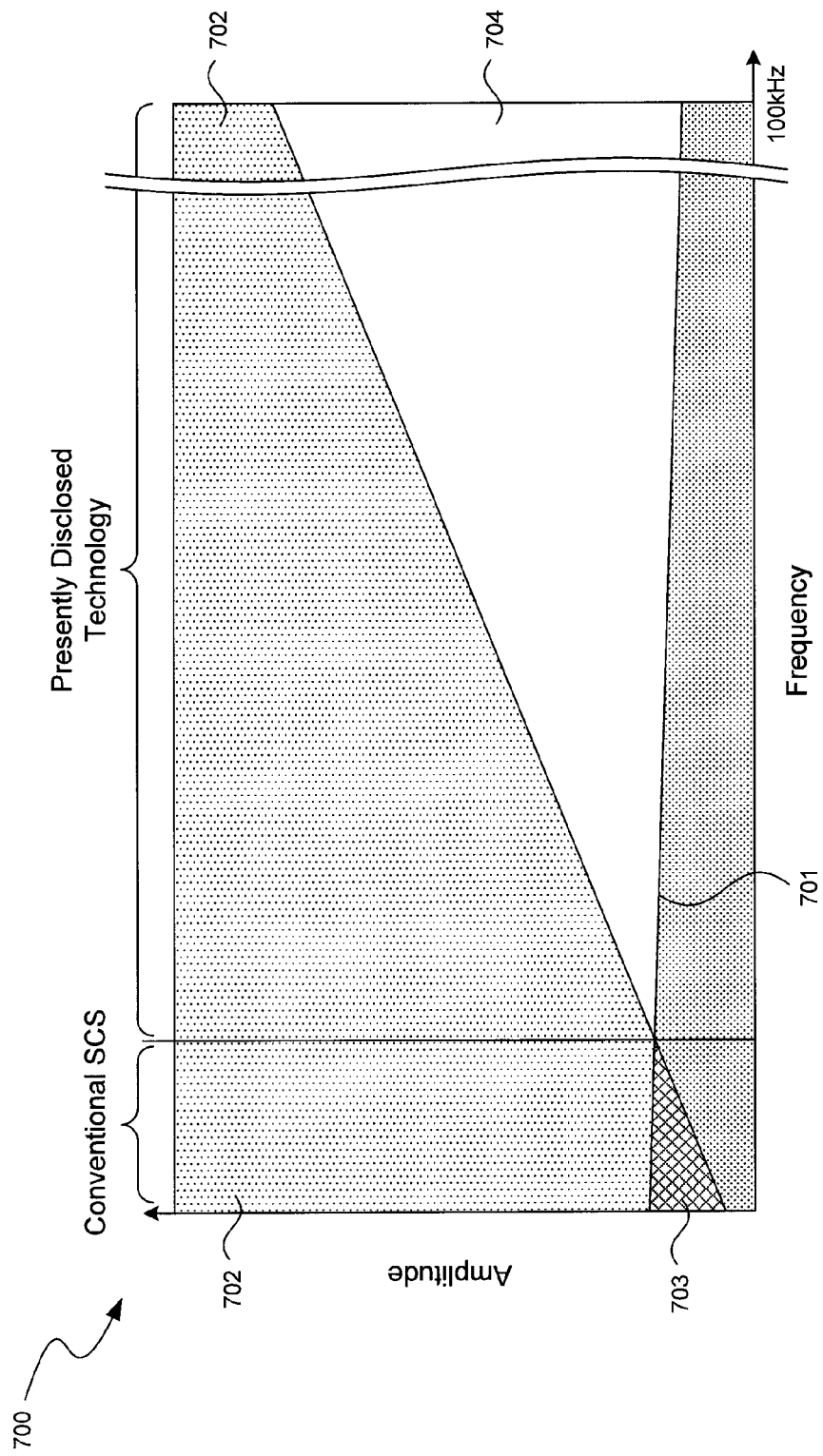
FIG. 7 is a graphical illustration comparing modulation amplitude effects for standard SCS with those for the presently disclosed technology.

FIG. 7 illustrates a graph 700 identifying amplitude as a function of frequency for conventional SCS and for therapy in accordance with embodiments of the presently disclosed technology. Threshold amplitude level 701 indicates generally the minimum amplitude necessary to achieve a therapeutic effect, e.g., pain reduction. A first region 702 corresponds to amplitudes, as a function of frequency, for which the patient senses paresthesia induced by the therapy, pain induced by the therapy, and/or uncomfortable or undesired muscle stimulation induced by the therapy. As shown in FIG. 7, at conventional SCS frequencies, the first region 702 extends below the threshold amplitude level 701. Accordingly, a second region 703 indicates that the patient undergoing conventional SCS therapy typically detects paresthesia, other sensory effects, and/or undesirable motor effects below the amplitude necessary to achieve a therapeutic effect. One or more of these side effects are also present at amplitudes above the threshold amplitude level 701 required to achieve the therapeutic effect. By contrast, at frequencies associated with the presently disclosed technology, a "window" 704 exists between the threshold amplitude level 701 and the first region 702. Accordingly, the patient can receive therapeutic benefits at amplitudes above the threshold amplitude level 701, and below the amplitude at which the patient may experience undesirable side effects (e.g., paresthesia, sensory effects and/or motor effects).

Although the presently disclosed therapies may allow the practitioner to provide modulation over a broader range of amplitudes, in at least some cases, the practitioner may not need to use the entire range. For example, as described above, the instances in which the patient may need to adjust the therapy may be significantly reduced when compared with standard SCS therapy because the presently disclosed therapy is relatively insensitive to patient position, posture and activity level. In addition to or in lieu of the foregoing effect, the amplitude of the signals applied in accordance with the presently disclosed techniques may be lower than the amplitude associated with standard SCS because the presently disclosed techniques may target neurons that are closer to the surface of the spinal cord. For example, it is believed that the nerve fibers associated with low back pain enter the spinal cord between T9 and T12 (inclusive), and are thus close to the spinal cord surface at these vertebral locations. Accordingly, the strength of the therapeutic signal (e.g., the current amplitude) can be modest because the signal need not penetrate through a significant depth of spinal cord tissue to have the intended effect. Such low amplitude signals can have a reduced (or zero) tendency for triggering side effects, such as unwanted sensory and/or motor responses. Such low amplitude signals can also reduce the power required by the implanted pulse generator, and can therefore extend the battery life and the associated time between recharging and/or replacing the battery.

Yet another expected benefit of providing therapy in accordance with the presently disclosed parameters is that the practitioner need not implant the lead with the same level of precision as is typically required for standard SCS lead placement. For example, while at least some of the foregoing results were obtained for patients having two leads (one positioned on either side of the spinal cord midline), it is expected that patients will receive the same or generally similar pain relief with only a single lead placed at the midline. Accordingly, the practitioner may need to implant only one lead, rather than two. It is still further expected that the patient may receive pain relief on one side of the body when the lead is positioned offset from the spinal cord midline in the opposite direction. Thus, even if the patient has bilateral pain, e.g., with pain worse on one side than the other, the patient's pain can be addressed with a single implanted lead. Still further, it is expected that the lead position can vary laterally from the anatomical and/or physiological spinal cord midline to a position 3-5 mm. away from the spinal cord midline (e.g., out to the dorsal root entry zone or DREZ). The foregoing identifiers of the midline may differ, but the expectation is that the foregoing range is effective for both anatomical and physiological identifications of the midline, e.g., as a result of the robust nature of the present therapy. Yet further, it is expected that the lead (or more particularly, the active contact or contacts on the lead) can be positioned at any of a variety of axial locations in a range of about T8-T12 in one embodiment, and a range of one to two vertebral bodies within T8-T12 in another embodiment, while still providing effective treatment for low back pain. Accordingly, the practitioner's selected implant site need not be identified or located as precisely as it is for standard SCS procedures (axially and/or laterally), while still producing significant patient benefits. In particular, the practitioner can locate the active contacts within the foregoing ranges without adjusting the contact positions in an effort to increase treatment efficacy and/or patient comfort. In addition, in particular embodiments, contacts at the foregoing locations can be the only active contacts delivering therapy to the patient. The foregoing features, alone or in combination, can reduce the amount of time required to implant the lead, and can give the practitioner greater flexibility when implanting the lead. For example, if the patient has scar tissue or another impediment at a preferred implant site, the practitioner can locate the lead elsewhere and still obtain beneficial results.

Still another expected benefit, which can result from the foregoing observed insensitivities to lead placement and signal amplitude, is that the need for conducting a mapping procedure at the time the lead is implanted may be significantly reduced or eliminated. This is an advantage for both the patient and the practitioner because it reduces the amount of time and effort required to establish an effective therapy regimen. In particular, standard SCS therapy typically requires that the practitioner adjust the position of the lead and the amplitude of the signals delivered by the lead, while the patient is in the operating room reporting whether or not pain reduction is achieved. Because the presently disclosed techniques are relatively insensitive to lead position and amplitude, the mapping process can be eliminated entirely. Instead, the practitioner can place the lead at a selected vertebral location (e.g., about T8-T12) and apply the signal at a preselected amplitude (e.g., 1 to 2 mA), with a significantly reduced or eliminated trial-and-error optimization process (for a contact selection and/or amplitude selection), and then release the patient. In addition to or in lieu of the foregoing effect, the practitioner can, in at least some embodiments, provide effective therapy to the patient with a simple bipole arrangement of electrodes, as opposed to a tripole or other more complex arrangement that is used in existing systems to steer or otherwise direct therapeutic signals. In light of the foregoing effect(s), it is expected that the time required to complete a patient lead implant procedure and select signal delivery parameters can be reduced by a factor of two or more, in particular embodiments. As a result, the practitioner can treat more patients per day, and the patients can more quickly engage in activities without pain.

The foregoing effect(s) can extend not only to the mapping procedure conducted at the practitioner's facility, but also to the subsequent trial period. In particular, patients receiving standard SCS treatment typically spend a week after receiving a lead implant during which they adjust the amplitude applied to the lead in an attempt to establish suitable amplitudes for any of a variety of patient positions and patient activities. Because embodiments of the presently disclosed therapy are relatively insensitive to patient position and activity level, the need for this trial and error period can be reduced or eliminated.

Still another expected benefit associated with embodiments of the presently disclosed treatment is that the treatment may be less susceptible to patient habituation. In particular, it is expected that in at least some cases, the high frequency signal applied to the patient can produce an asynchronous neural response, as is disclosed in co-pending U.S. application Ser. No. 12/362,244, incorporated herein by reference. The asynchronous response may be less likely to produce habituation than a synchronous response, which can result from lower frequency modulation.

Yet another feature of embodiments of the foregoing therapy is that the therapy can be applied without distinguishing between anodic contacts and cathodic contacts. As described in greater detail in U.S. application Ser. No. 12/765,790, incorporated herein by reference, this feature can simplify the process of establishing a therapy regimen for the patient. In addition, due to the high frequency of the waveform, the adjacent tissue may perceive the waveform as a pseudo steady state signal. As a result of either or both of the foregoing effects, tissue adjacent both electrodes may be beneficially affected. This is unlike standard SCS waveforms for which one electrode is consistently cathodic and another is consistently anodic.

In any of the foregoing embodiments, aspects of the therapy provided to the patient may be varied, while still obtaining beneficial results. For example, the location of the lead body (and in particular, the lead body electrodes or contacts) can be varied over the significant lateral and/or axial ranges described above. Other characteristics of the applied signal can also be varied. For example, the signal can be delivered at a frequency of from about 1.5 kHz to about 100 kHz, and in particular embodiments, from about 1.5 kHz to about 50 kHz. In more particular embodiments, the signal can be provided at frequencies of from about 3 kHz to about 20 kHz, or from about 3 kHz to about 15 kHz, or from about 5 kHz to about 15 kHz, or from about 3 kHz to about 10 kHz. The amplitude of the signal can range from about 0.1 mA to about 20 mA in a particular embodiment, and in further particular embodiments, can range from about 0.5 mA to about 10 mA, or about 0.5 mA to about 4 mA, or about 0.5 mA to about 2.5 mA. The amplitude of the applied signal can be ramped up and/or down. In particular embodiments, the amplitude can be increased or set at an initial level to establish a therapeutic effect, and then reduced to a lower level to save power without forsaking efficacy, as is disclosed in pending U.S. application Ser. No. 12/264,536, filed Nov. 4, 2008, and incorporated herein by reference. In particular embodiments, the signal amplitude refers to the electrical current level, e.g., for current-controlled systems. In other embodiments, the signal amplitude can refer to the electrical voltage level, e.g., for voltage-controlled systems. The pulse width (e.g., for just the cathodic phase of the pulses) can vary from about 10 microseconds to about 333 microseconds. In further particular embodiments, the pulse width can range from about 25 microseconds to about 166 microseconds, or from about 33 microseconds to about 100 microseconds, or from about 50 microseconds to about 166 microseconds. The specific values selected for the foregoing parameters may vary from patient to patient and/or from indication to indication and/or on the basis of the selected vertebral location. In addition, the methodology may make use of other parameters, in addition to or in lieu of those described above, to monitor and/or control patient therapy. For example, in cases for which the pulse generator includes a constant voltage arrangement rather than a constant current arrangement, the current values described above may be replaced with corresponding voltage values.

In at least some embodiments, it is expected that the foregoing amplitudes will be suprathreshold. It is also expected that, in at least some embodiments, the neural response to the foregoing signals will be asynchronous, as described above. Accordingly, the frequency of the signal can be selected to be higher (e.g., between two and ten times higher) than the refractory period of the target neurons at the patient's spinal cord, which in at least some embodiments is expected to produce an asynchronous response.

Patients can receive multiple signals in accordance with still further embodiments of the disclosure. For example, patients can receive two or more signals, each with different signal delivery parameters. In one particular example, the signals are interleaved with each other. For instance, the patient can receive 5 kHz pulses interleaved with 10 kHz pulses. In other embodiments, patients can receive sequential "packets" of pulses at different frequencies, with each packet having a duration of less than one second, several seconds, several minutes, or longer depending upon the particular patient and indication.

From the foregoing, it will be appreciated that specific embodiments of the technology have been described herein for purposes of illustration, but that various modifications may be made without deviating from the present disclosure. For example, therapies described in the context of particular vertebral locations to treat low back pain may be applied to other vertebral levels to treat other types of pain. In still further embodiments, the therapeutic effect can include indications in addition to or in lieu of pain. Certain aspects of the disclosure described in the context of particular embodiments may be combined or eliminated in other embodiments. For example, patients can receive treatment at multiple vertebral levels and/or via leads or other signal delivery devices positioned at multiple locations. The foregoing mechanisms of action are believed to account for the patient responses observed during treatment in accordance with the presently disclosed technology; however, other mechanisms or processes may operate in addition to or in lieu of the foregoing mechanisms in at least some instances. Further, while advantages associated with certain embodiments have been described in the context of those embodiments, other embodiments may also exhibit such advantages, and not all embodiments need necessarily exhibit such advantages to fall within the scope of the present technology. Accordingly, the present disclosure and associated technology can encompass other embodiments not expressly shown or described herein. The following examples provide additional embodiments of the technology.

We claim:

1. A patient treatment method, comprising:
   selecting a neural modulation site to include a dorsal horn of a spinal cord of the patient; and
   desensitizing a wide dynamic range neuron at the dorsal horn by applying to the dorsal horn a non-paresthesia producing neural modulation signal having a signal frequency in a range of from about 1.5 kHz to about 100 kHz, to address patient pain, the pain being addressed for a period of time after at least reducing an intensity of the signal, the period of time being at least one tenth of one second.

2. The method of claim 1 wherein the signal frequency is in a range of from about 3 kHz to about 100 kHz.

3. The method of claim 1 wherein the period of time is up to about one day.

4. The method of claim 1, further comprising reducing afferent signals transmitted by neurons at the dorsal horn.

5. The method of claim 1, further comprising programming a patient therapy device to deliver the neural modulation signal in accordance with selected parameters.

6. The method of claim 1 wherein the period of time is a period of time after ceasing delivery of the signals.

7. The method of claim 1 wherein the pain is addressed for the period of time after at least reducing the intensity of the signal without a patient-detectable change in a therapeutic efficacy of the signal.

8. The method of claim 1 wherein the pain is addressed for the period of time after at least reducing the intensity of the signal without a decrease in a pain-reducing effect of the signal when the signal intensity is reduced.

9. The method of claim 1 wherein the signal has pulses with a pulse width of from about 33 microseconds to about 100 microseconds.

10. A patient treatment method, comprising:
   selecting a neural modulation site to include a dorsal horn of a spinal cord of the patient; and
   desensitizing a wide dynamic range neuron at the dorsal horn by applying to the dorsal horn a non-paresthesia producing neural modulation signal having a frequency of from about 3 kHz to about 100 kHz to reduce patient pain.

11. The method of claim 10 wherein the neural modulation signal has at least approximately no effect on the patient's normal sensory functions.

12. The method of claim 10 wherein the neural modulation signal has at least approximately no effect on the patient's normal motor activity.

13. The method of claim 10 wherein the neural modulation signal has at least approximately no effect on the patient's normal proprioception.

14. The method of claim 10 wherein the signal frequency is in a range of from about 3 kHz to about 20 kHz.

15. The method of claim 10 wherein the signal frequency is in a range of from about 3 kHz to about 15 kHz.

16. The method of claim 10 wherein the signal frequency is in a range of from about 5 kHz to about 15 kHz.

17. The method of claim 10 wherein the signal frequency is in a range of from about 3 kHz to about 10 kHz.

18. The method of claim 10 wherein the signal has pulses with a pulse width of from about 10 microseconds to about 333 microseconds.

19. The method of claim 10 wherein the signal has pulses with a pulse width of from about 33 microseconds to about 100 microseconds.

20. The method of claim 10 wherein the signal has a frequency of from about 5 kHz to about 15 kHz and a pulse width of from about 25 microseconds to about 166 microseconds.

* * * * *